United States Patent [19]

Howell et al.

[11] Patent Number: 5,223,405
[45] Date of Patent: Jun. 29, 1993

[54] SAMPLING BY PRESSING BETWEEN ADSORBENT AND SUBSTRATE SURFACES

[75] Inventors: Peter J. Howell; D. Gavin Rose; David H. Mitchell, all of Edinburgh, Scotland

[73] Assignee: The Secretary of State for Scotland, Edinburgh, Scotland

[21] Appl. No.: 579,103

[22] Filed: Sep. 5, 1990

Related U.S. Application Data

[63] Continuation of Ser. No. 154,299, Feb. 10, 1988, abandoned.

[30] Foreign Application Priority Data

Feb. 11, 1987 [GB] United Kingdom ............... 8703081

[51] Int. Cl.⁵ .................................. C12Q 1/24
[52] U.S. Cl. ........................... 435/30; 435/29; 435/292; 435/287; 128/749; 128/738; 422/99
[58] Field of Search ............ 422/56, 58, 61, 100, 422/102; 435/30, 34, 292, 293, 294, 299, 300, 301; 73/863.21, 863.23; 128/749, 738; 606/205; 436/808

[56] References Cited

U.S. PATENT DOCUMENTS

| | | | |
|---|---|---|---|
| 2,292,450 | 8/1942 | Kohn | 435/30 X |
| 3,785,930 | 1/1974 | Ellis | 435/30 X |
| 3,843,452 | 10/1974 | Freale et al. | 435/294 |
| 4,055,394 | 10/1977 | Friedman et al. | 436/809 X |
| 4,225,557 | 9/1980 | Hartl et al. | 422/56 |
| 4,368,272 | 1/1983 | Kashket | 435/30 X |
| 4,476,226 | 10/1984 | Hansen et al. | 435/30 X |
| 4,540,659 | 9/1985 | Litman et al. | 436/824 X |
| 4,582,795 | 4/1986 | Shibaya et al. | 435/34 |
| 4,673,638 | 6/1987 | Grosch et al. | 435/30 X |
| 4,713,344 | 12/1987 | Markhart, III | 435/30 X |
| 4,789,629 | 10/1988 | Baker et al. | 435/7 |
| 4,826,759 | 5/1989 | Guire et al. | 435/4 |
| 4,826,772 | 5/1989 | Meathrel | 436/93 |
| 4,839,297 | 6/1989 | Freitag et al. | 436/170 |
| 4,963,325 | 10/1990 | Lennon et al. | 422/61 |

FOREIGN PATENT DOCUMENTS 0146143  6/1985  European Pat. Off. ............ 435/299

*Primary Examiner*—Robert J. Warden
*Assistant Examiner*—T. A. Trembley
*Attorney, Agent, or Firm*—Fish & Richardson

[57] ABSTRACT

A sample of a biological tissue and/or fluid, particularly plant sap, may be taken by placing biological tissue such as a leaf between a layer which is adsorbent for detectable biological material (for example nitrocellulose) and a substrate and applying pressure to urge the adsorbent layer and the substrate towards each other, thereby causing detectable biological material to be adsorbed on the adsorbent layer. The invention thus provides a convenient method of obtaining, securing and transporting small samples of plant sap or other fluid or tissue to the laboratory for such purposes as analysis for plant viruses and other organisms.

8 Claims, 1 Drawing Sheet

SAMPLING BY PRESSING BETWEEN ADSORBENT AND SUBSTRATE SURFACES

This is a continuation of application Ser. No. 07/154,299, filed Feb. 10, 1988, now abandoned.

This invention relates to a method of sampling tissue and/or fluids of biological origin, particularly of plant origin, and to a device suitable for use in such a method.

The need to sample plant tissue and/or fluids stems from, among other things, the desirability of being able to diagnose and monitor plant disease. The economic implications of being able accurately and quickly to diagnose and monitor plant diseases need no emphasis.

Many diagnostic or other monitoring tests for plant disease require relatively complex equipment that is not conveniently or practicably transportable in the field. Samples of plant tissue and/or fluid therefore needs to be taken back to the laboratory, where they may undergo conventional biochemical analyses or some of the more recently developed tests such as immunodiagnostic tests using for example monoclonal antibodies or nucleic acid analysis using for example DNA or RNA probes or sequencing methodology.

For the purposes of, for example, laboratory analysis, there is therefore a need for a convenient method of obtaining, securing and transporting small samples of plant sap or other fluid or tissue to the laboratory for such purposes as analysis for plant viruses and other organisms. It is envisaged that an appropriate method could also find application in the sampling of animal tissue and/or fluid.

According to a first aspect of the present invention, there is provided a method of taking a sample of a plant or other biological tissue and/or fluid, the method comprising placing biological tissue between a layer which is adsorbent for detectable biological material and a substrate and applying pressure to urge the adsorbent layer and the substrate toward each other, thereby causing detectable biological material to be adsorbed on the adsorbent layer.

Detectable biological material may thus in effect be immobilised by the adsorbent layer, with which it may form an interaction which may be unaffected by subsequent analysis or processing. The sample may be described as being 'captured' by the adsorbent layer. The detectable biological material will often be antigenic (e.g. proteinaceous) material allowing for subsequent immunological detection. However, other detectable material, for example, nucleic acid, may also be adsorbed. Nucleic acid may be detectable by sequencing and/or hybridisation. Proteins may be analysed by amino acid analysis.

It is very much preferred that a second substrate be provided the other side of the adsorbent layer from the first substrate. Pressure can then be applied to urge the two substrates towards each other, thereby causing the desired adsorption of protein and/or nucleic acid.

More than one layer may be provided: for example, the biological tissue and/or fluid may in use be sandwiched between adsorbent layers.

The combination of the adsorbent layer and the substrate(s) will for convenience be referred to as a "device".

Although it is usual for only small volumes of liquid to be involved in sampling, in view of the fact that detectable biological material may be detected in less than 1 microliter of, for example, plant sap, the adsorbent layer is preferably also absorbent so that the sample dries rapidly. Rapid drying is useful as it allows the device to be handled with a reduced risk of contamination. The chances of sample degradation by enzymic reaction are also reduced. For the same reasons a small sample size is preferred.

The adsorbent layer may be in the form of a sheet. When there are two substrates, they are preferably hinged together, either at a common edge or along some other line. The adsorbent sheet can be retained on one of the substrates by, for example, adhesive, although any suitable retaining means, such as stapling, tacking or pinning, can be used.

When there are two substrates, the surface of at least one of them that faces the other (the inner surface) may be coated with adsorbent material. This arrangement is usually an alternative to having a separate sheet of adsorbent material.

The preferred material for the adsorbent layer is nitrocellulose, which has the ability to adsorb nucleic acids and proteins. It is this property of nitrocellulose which underlies the "dot blot" method of polyvirus detection described by Berger et al (Virol. Methods 12 (1985) 31-39). However, although the use of nitrocellulose is preferred for its affinity for proteins and nucleic acids, it is not necessarily the only suitable material, as other adsorbent materials may be able to capture sufficient detectable biological material from, for example, plant tissue and/or fluid (such as sap) to enable effective analysis to take place in the laboratory. Examples of other suitable but less preferred adsorbent materials include adsorbent paper (such as blotting paper or filter paper), cotton wool, cellulose wadding and woven or non-woven fabrics, lint and synthetic material (such as nylon) for example in the form of a membrane. In some circumstances the adsorbent layer may be provided by the surface of at least one of the substrates. More than one adsorbent layer may be provided if desired.

When the adsorbent layer is coated on a substrate it may be applied as a liquid solution or suspension. For example, nitrocellulose may be dissolved in an appropriate solvent.

The two substrates are for convenience of identical or similar construction as each other. They will generally be inert, and it is preferred that they be generally less adsorbent than the adsorbent layer, so as to enhance the efficacy of the adsorbent layer. It is also preferred that the substrates be flexible, and to achieve this and other desirable characteristics, it has been found convenient to make the substrates at least partially of plastics material or paper or cardboard coated with a plastics or other inert layer, at least in the region of the adsorbent layer, which in turn, as described above, may be coated on the substrate(s). The substrates are preferably in the form of sheets.

One or both of the surfaces which in use, are in contact with the tissue and/or fluid (that is, the specimen) may be made abrasive or otherwise adapted to assist in crushing.

One of the substrates, for example the one to which an adsorbent sheet is not attached, may be at least partially removable from the device, so that laboratory reagents may during subsequent analysis be readily applied to the adsorbent layer. When the substrate is a sheet of, for example, plastics material or coated paper or cardboard, it may conveniently be perforated so that a portion of it can easily be removed. For even easier accessibility of the adsorbent layer to reagents, both substrates may be removable (at least in part) for example by virtue of being perforated.

If there are two adsorbent layers (which may be coated each onto one substrate), taking the sample will result in two almost identical samples. The two samples may be processed together, or one may be retained as a check test.

The device is preferably provided with data recording means, for example in the form of an identification label on which can be recorded data relevant to the tissue being sampled. Such data might include the name and address of the person for whom the sample is to be analysed, a serial number, the data, the type(s) of analysis to which the sample is to be submitted and/or possibly an indication of any suspected infection, the causative agent of which is to be looked for on analysis. The data recordal means can conveniently be provided as or on an extension of one or both of the substrates. The two substrates may therefore be fixed together in a region away from the adsorbent layer.

When at least one of the substrates is coated with the adsorbent layer, identification data (such as a serial number) may be provided on a coated and detachable portion of the substrate (or of one or each of the substrates) and repeated in an identification label. This will allow remote processing of the functional portion of the device. After analysis, results can be identified by matching the identification data on the coated and detachable portion with the data on the label. This can lead to a reduced size of the portion subjected to analysis and the possibility of complete immersion of the coated detached area without all the information on the label being subjected to the risk of becoming illegible during the analysis process.

The overall size of the device need not be large. In the case of substantially planar substrates and adsorbent layer, the thickness need only be in the order of 0.5 to 5 mm, for example about 1 or 2 mm. The length, including an identification label, can vary, for example from 50 mm to 200 mm. A convenient length is about 110 mm. The width may vary from 10 to 50 mm, although about 25 mm has been found to be convenient. With the convenient proportions just described, the layer of adsorbent material may be about 20×15 mm, although its size will generally be chosen with regard being had to whatever size of substrates are used.

Although dimensions have been given to illustrate convenient size ranges, they are not absolutely limiting. The lower size limit of the device will generally be that which allows reliable sampling without contamination by either the operator or any device giving a mechanical advantage (for example a pair of pliers, tweezers or forceps) which he may be using to apply pressure to the device. Given this, it is generally preferable to have the device as small as possible both to allow sampling of small organisms and to economise on test reagents. The upper size limit may be determined only by convenience; for example it may be wished to use the device to take a sap sample from the whole (or a large part of the) area of a large leaf.

According to a second aspect of the present invention there is provided a biological tissue and/or fluid sampling device comprising a layer of nitrocellulose sandwiched between two substrates, the nitrocellulose and the substrates being held together in such a way that biological, for example plant, tissue can be removably inserted between the nitrocellulose and at least one of the substrates.

Other preferred features of the second aspect of the invention are as for the first aspect mutatis mutandis.

BRIEF DESCRIPTION OF THE DRAWINGS

For a better understanding of the present invention and to show how it may be put into effect, reference will now be made to the accompanying drawing, in which.

Figure 1:
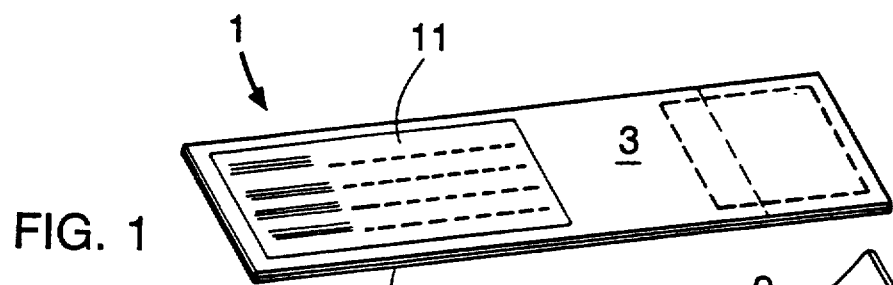
FIG. 1 is a perspective view of the device in accordance with the invention ready for use.
Figure 2:
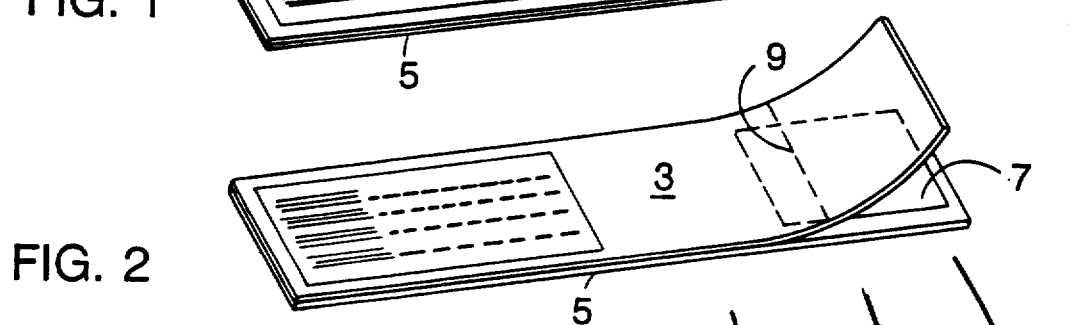
FIG. 2 is a perspective view of the same device shown in FIG. 1 (with some features omitted for clarity), the substrate being splayed apart to show the absorbent layer in between them.

Referring now to the drawings, a plant sampling device 1 in accordance with the invention comprises two thin sheets of inert plastics material The upper sheet 3 and the lower sheet 5 form inert substrates and are bonded together at their left hand ends for about three quarters of their length. The last 15 mm or so at the right hand end are not bonded together, so that they may hinge apart to reveal a nitrocellulose layer 7 which is located between them and bonded to the lower plastics layer 5. (In an alternative embodiment, the nitrocellulose layer may be coated upon one or both of the sheets 3 and 5.)

The upper sheet 3 has a line of perforations 9 extending across its width in the region of the nitrocellulose absorbent layer 7, for a purpose that will become clear later.

The upper plastics sheet 1 is provided with an identification label 11, for recording data indicative of the sample to be taken.

Figure 3:
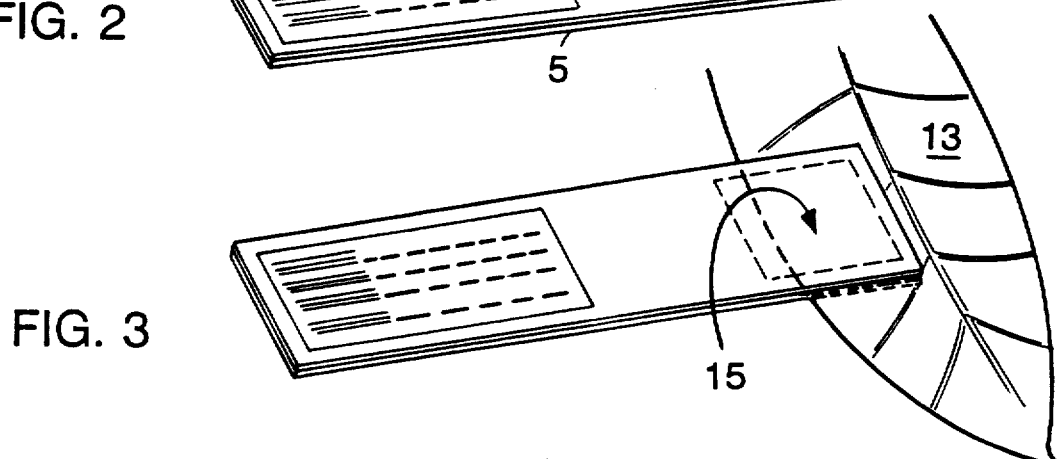
FIG. 3 shows the device shown in FIG. 1 in use taking a sample from a plant leaf.
Figure 4:
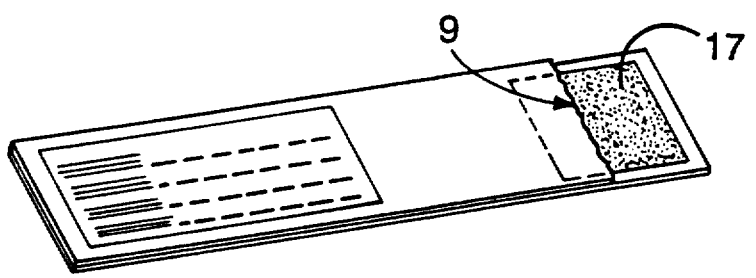
FIG. 4 shows the same device after the sample has been taken and ready for laboratory processing.

The use of the device can be seen in FIG. 3. The right hand end is splayed apart to allow its location either side of the margin of a leaf 13 or other plant organ to be sampled. The leaf is thus located between the nitrocellulose adsorbent layer 7 and the upper plastics layer 3. Pressure is then applied to the outside of the upper and lower plastics layers 3 and 5 generally at point 15. By the application of pressure, a small quantity of plant sap (possibly in conjunction with plant tissue) is expressed from the leaf 13 or other organ and captured on the nitrocellulose layer 7. Pressure may be applied by hand or with the aid of a device giving a mechanical advantage, such as a pair of pliers.

The texture of the surface of the device at either side of the leaf may be so adapted (for example by being roughened) as to assist in the crushing of the leaf.

If the identification label 11 has not previously been made use of, details of the sample can then be written on the label, which then can be despatched by post or any other mode of transport to a servicing laboratory for the processing of the sample to detect, for example, viruses or other pathogens.

In the laboratory, the upper plastics layer 3 can be torn along the perforation 9 to expose a substantial portion of the nitrocellulose layer 7 and the sap 17 on the nitrocellulose layer. The sap is therefore exposed for chemical analysis, and can be processed in any way and the results recorded and reported in the usual way.

What is claimed is:

1. A method for directly securing a sample of detectable biological material from an in vivo biological source which must be crushed to release said detectable biological material, the method comprising providing a sampling device comprising a first substrate defining a first surface, a second substrate defining a second surface opposed to said first surface, said first substrate and said second substrate joined together in a region spaced from said first and second surfaces, and an adsorbent layer for detectable biological material disposed generally in a region between said first surface and said second surface, placing said sampling device with said adsorbent layer which is adsorbent for detectable biological material and said first or second substrate about an in vivo biological source from which a sample of detectable biological material is to be obtained so that the source is engaged by a surface of said layer and a surface of said first or second substrate, crushing said in vivo biological source by applying pressure to urge the adsorbent layer and the said first or second substrate towards each other about the in vivo biological source, thereby causing a sample of detectable biological material to be released from the in vivo biological source and adsorbed on the adsorbent layer, and providing an additional layer adsorbent for detectable biological material, said additional layer being disposed generally in the region between said adsorbent layer and said first or second substrate.

2. A method as claimed in claim 1 comprising the further step of obtaining a detectable biological material in the form of plant sap or a residue of dried plant sap.

3. A method as claimed in claim 1 comprising the further step of providing said sampling device with said first substrate and said second substrate hinged together.

4. The method as claimed in claim 1 further comprising providing, as the adsorbent layer, nitrocellulose.

5. The method as claimed in claim 1 further comprising providing one or both substrates as a flexible member.

6. A method for directly securing a sample of detectable biological material from an in vivo biological source which must be crushed to release said detectable biological material, the method comprising providing a sampling device comprising a first substrate defining a first surface, a second substrate defining a second surface opposed to said first surface, said first substrate and said second substrate joined together in a region spaced from said first and second surfaces, and an adsorbent layer for detectable biological material disposed generally in a region between said first surface and said second surface, placing said sampling device with said adsorbent layer which is adsorbent for detectable biological material and said first or second substrate about an in vivo biological source from which a sample of detectable biological material is to be obtained so that the in vivo biological source is engaged by a surface of said adsorbent layer and a surface of said first or second substrate, crushing said in vivo biological source by applying pressure to urge the adsorbent layer and the said first or second substrate towards each other about the in vivo biological source, thereby causing a sample of detectable biological material to be released from the in vivo biological source and adsorbed on the adsorbent layer, and providing at least one said surface, which, in use, is in contact with the detectable biological material, roughened for facilitating crushing of the sample when pressure is applied urging the adsorbent layer and said first or second substrate towards each other.

7. A method as claimed in claim 6 comprising the further step of providing said sampling device with at least one of said first substrate and said second substrate being at least partially removable.

8. A method as claimed in claim 6 comprising the further step of providing data recording means comprising an identification label in association with at least one of said adsorbent layer and said first or second substrate.

* * * * *